Figure 1:
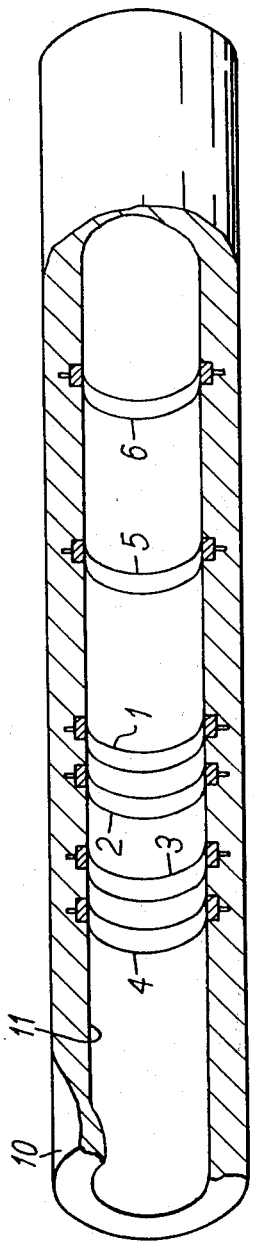

United States Patent [19]

Warmoth et al.

[11] 3,993,945

[45] Nov. 23, 1976

[54] MEASURING CELLS FOR MEASURING ELECTRICAL CONDUCTIVITY OF LIQUIDS

[75] Inventors: Denis Warmoth; Kenneth James Porter, both of Hitchin, England

[73] Assignee: George Kent Limited, England

[22] Filed: July 21, 1975

[21] Appl. No.: 597,915

[30] Foreign Application Priority Data

Aug. 2, 1974  United Kingdom............... 34210/74

[52] U.S. Cl. ........................... 324/30 B; 324/30 R; 204/195 F
[51] Int. Cl.[2] ......................................... G01N 27/42
[58] Field of Search.................... 204/195 R, 195 F; 324/30 R, 30 B, 30 A

[56] References Cited
UNITED STATES PATENTS

| | | | |
|---|---|---|---|
| 3,283,240 | 11/1966 | Spady................................ | 324/30 B |
| 3,701,006 | 10/1972 | Volkel............................... | 324/30 B |
| 3,714,555 | 1/1973 | Greer................................ | 324/30 B |

Primary Examiner—R. V. Rolinec
Assistant Examiner—Michael J. Tokar
Attorney, Agent, or Firm—Browdy and Neimark

[57] ABSTRACT

A measuring cell for measuring electrical conductivity of liquids having a bore which in operation is contacted by a liquid, the conductivity of which is to be measured and a plurality of electrodes spaced along the bore and forming part of the bore surface, the electrodes being of coaxial annular form and including a first and a fourth electrode which constitute current electrodes for connection to a controllable AC current supply, a second and third electrode between the current electrodes and constituting voltage electrodes for connection to a high input impedance amplifier provided with means for employing the amplifier output to control the AC current supply to maintain sensibly constant the voltage at the voltage electrodes and a fifth electrode of annular form coaxial with the first to fourth electrodes and for connection to the first electrode by way of a buffer amplifier presenting a high impedance to the first electrode and a low impedance to the fifth electrode and located on the side of the first electrode remote from the fourth and voltage electrodes.

13 Claims, 1 Drawing Figure

MEASURING CELLS FOR MEASURING ELECTRICAL CONDUCTIVITY OF LIQUIDS

This invention relates to measuring cells for measuring electrical conductivity of liquids. More particularly the invention relates to such measuring cells of the kind comprising a body of electrically insulating material having a bore which in operation is contacted by liquid the conductivity of which is to be measured by the cell and plurality of electrodes spaced along the bore and embedded in the insulating material and forming part of the surface of the bore.

Measuring cells of the kind referred to are hereinafter identified as measuring cells "of the kind set forth."

In British Patent Specification No. 869,226 a measuring cell of the kind set forth is described in which inner surfaces of the electrodes, which are of annular form, constitute part of the bore and are contiguous with the surface of the bore formed by the insulating material.

It is well known to provide measuring cells of the kind set forth having four annular electrodes, the outer electrodes being current electrodes and connected to a source of alternating current and the inner electrodes being voltage electrodes. A cell of this form can be used in either a constant current or a constant voltage mode. In the constant current mode, a constant a.c. current is applied to the outer or current electrodes and the voltage at the inner or voltage electrodes measured by a high input impedance a.c. voltmeter is a measure of the electrical conductivity of the liquid in the cell. The voltmeter reading is, however, inversely proportional to the measured conductivity so that the instrument does not give a direct reading of conductivity and this is undesirable. In the constant voltage mode of operation current is driven into the outer current electrodes from the output which is of variable amplitude and fixed frequency, suitably, of a voltage controlled generator. The voltage measured across the voltage electrodes is dependent upon the current from he generator and the conductivity of the liquid in the cell. This voltage is amplified by a high input impedance amplifier the output of which is supplied to a comparator where it is compared with a reference signal. The output of the comparator is applied to the voltage controlled generator output in such a manner as to drive current through the current electrodes of a magnitude to maintain a constant voltage at the voltage electrodes. The driven current under such circumstances is directly proportional to the electrical conductivity of the liquid within the dynamic amplitude range of the voltage controlled generator.

When fouling occurs at the current electrode surfaces resulting in additional impedance at the liquid-/electrode interface, because negligible current is drawn from the voltage electrodes, the voltage at the voltage electrodes will, within limits, remain unaffected thus assuring that the current is correct for a particular value of conductivity whilst the voltage across the current electrodes may increase due to increased impedance arising from fouling. Correct operation is maintained as long as the fouling impedances on the current electrodes do not require an applied voltage at the current electrodes outside the dynamic amplitude range of the voltage controlled generator.

The constant voltage mode of operation has the advantage that it is a direct reading system.

It is an object of the present invention to provide a measuring cell of the kind set forth for measuring electrical conductivity of liquids in which the flow of electrical currents out of the cell, for example to earthed metal pipe work connected to the cell, is inhibited since the outflow of such currents causes error in the measurement of conductivity of liquids in relation to which the cell is employed.

The present invention consists in a measuring cell of the kind set forth for measuring electrical conductivity of liquids, wherein there are provided electrodes of co-axial annular form, namely a first and a fourth electrode which constitute current electrodes for connection to a controllable a.c. current supply, a second and third electrode between the first and the fourth electrodes constituting voltage electrodes adapted for connection to a high input impedance amplifier means provided with means for employing the output of the amplifier means to control the a.c. current supply to maintain sensibly constant the voltage at the voltage electrodes, characterised by a fifth electrode of annular form co-axial with the first and fourth electrodes for connection to the first electrode by way of a buffer amplifier presenting a high impedance to the first electrode and a low impedance to the fifth electrode and located on the side of the first electrode remote from the fourth and voltage electrodes.

The invention further consists in a measuring cell of the kind set forth for measuring electrical conductivity of liquids, wherein there are provided electrodes of co-axial annular form, namely a first and fourth electrode which constitute current electrodes connected to a controllable a.c. current supply, a second and third electrode between the first and fourth electrodes constituting voltage electrodes, a high input impedance amplifier means connected to the voltage electrodes and with means for employing the output of the amplifier means to control the a.c. current supply to maintain sensibly constant the voltage at the voltage electrodes, and means for measuring the current supplied to the first and fourth electrodes by the controllable a.c. current supply, characterised by a fifth electrode of annular form co-axial with the first and fourth electrodes connected to the first electrode by way of a buffer amplifier presenting a high impedance to the first electrode and low impedance to the fifth electrode and located on the side of the first electrode remote from the fourth and voltage electrodes.

In a measuring cell according to the invention the fourth electrode is earthed and no current can flow between the first and fifth electrodes so that leakage current flow from the fifth electrode to surrounding earthed pipe work does not affect the liquid conductivity measurement.

For certain applications, especially medical applications, for example kidney machines, it is important to prevent outflow of current to earthed pipe work or the like. To this end there is advantageously provided a sixth electrode which is of annular form co-axial with the fifth electrode and located on the side thereof remote from the first to fourth electrodes, the sixth electrode being connected with the fourth electrode to earth. Thus, the sixth electrode provides an earth return path for leakage current flowing from the fifth electrode.

Preferably, the axial spacings between the first and fourth,, the first and fifth, and, the fifth and sixth electrodes are sensibly equal. Also, the voltage electrodes which are preferably of annular form, co-axial with the other electrodes are symmetrically located between the first and fourth electrodes and mutually spaced by half the spacing between the first and fourth electrodes.

Figure 2:
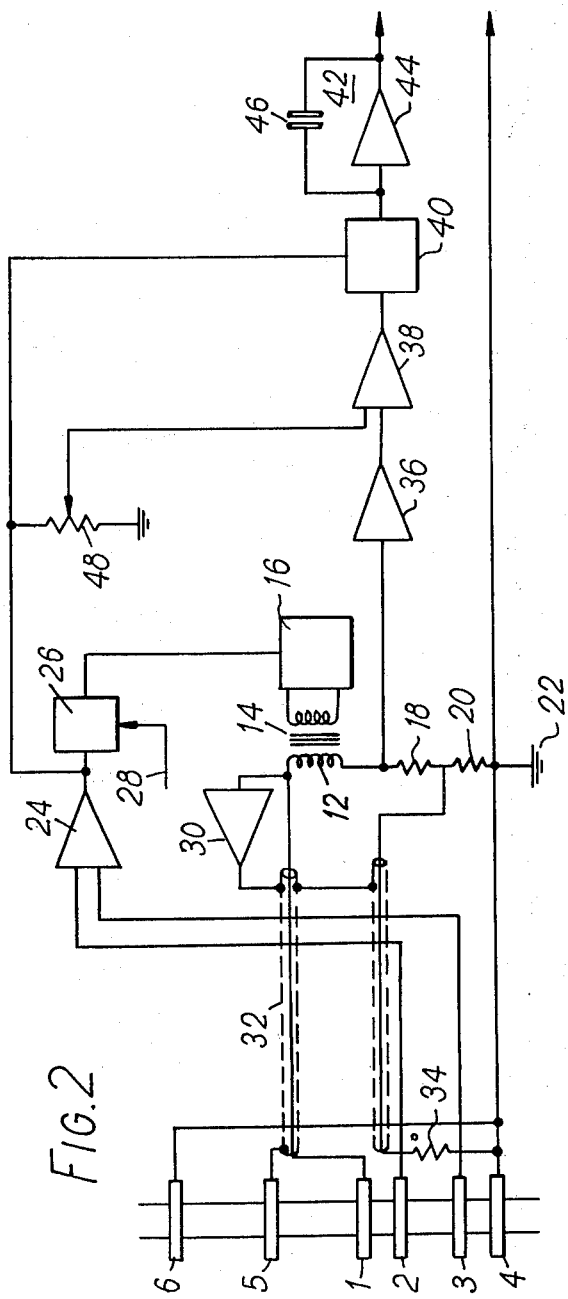

The invention will now be described, by way of example, with reference to the accompanying drawings, in which FIG. 1 is a perspective view partly in section illustrating the construction of a measuring cell according to the invention for measuring electrical conductivity of liquids, and, FIG. 2 is a block diagram of one form of circuit employing the cell illustrated in FIG. 1.

Referring first to FIG. 1 the measuring cell therein illustrated is constructed generally as described in British Patent Specification No. 869226 particularly with reference to the embodiment illustrated in FIG. 5 of that specification. The cell comprises a tube 10 of insulating material having a bore 11 there being embedded in the tube 10 electrodes 1 to 6 which are of co-axial annular form. The inner surfaces of electrodes 1 to 6 are disposed flush with and contiguous with the surface of the bore 11.

Electrodes 1 and 4 are current electrodes and electrodes 2 and 3 are voltage electrodes which are symmetrical with respect to and mutually spaced by half the spacing between electrodes 1 and 4. Electrode 5 is as more fully explained below a driven electrode and spaced from electrode 1 by the same spacing as obtains between electrodes 1 and 4. Electrode 6 is spaced from electrode 5 by the same amount as the spacing between electrodes 1 and 5. Electrode 6 is a screen electrode which is connected with electrode 4 to a common earth. Each of electrodes 1 to 6 has an electrical connecting lead (not shown) connected thereto and extending to the exterior of the tube 10.

Referring now to FIG. 2, electrodes 1 and 4 which are current electrodes are connected to the secondary coil 12 of an output transformer 14 of a voltage controlled generator 16 of variable amplitude and fixed frequency by way of series resistors 18 and 20, these resistors being connected between electrode 4 and the coil 12. The generator 16 constitutes a controllable a.c. supply for the current electrodes 1 and 4.

Electrode 6 is connected with electrode 4 to a common earth 22.

Voltage electrodes 2 and 3 are connected to the input of a high input impedance amplifier 24 the output of which is connected with a comparator 26 to which a reference signal from a source is supplied as indicated at 28. The error signal constituting the output of the comparator is supplied to the generator 16 and serves to control the amplitude of the generator output so as to maintain sensibly constant the voltage at the voltage electrodes 2 and 3.

The electrode 5 is connected to the output of a transformer 14 by way of a buffer amplifier 30 having a high input impedance and a low output impedance. The input of the amplifier 30 is thus connected to the secondary coil 12 whilst its output is connected to the electrode 5 by the screening 32 of the current cable which connects the coil 12 with the electrode 1.

Temperature compensation is achieved by the series resistors 18 and 20 and a thermistor 34 mounted in the conductivity cell and connected between the electrode 4 and the common point of resistors 18 and 20 the latter resistors serving as slope correction resistors and being mounted outside the cell.

As is well known in the art, conductivity measurement is referred to a standard temperature of 25° C. The current flowing through the thermistor 34 is proportional to conductivity and because of the negative resistance coefficient of the thermistor, the resistance thereof changes inversely proportionally with liquid temperature having a desired value at 25° C. The parallel resistor 20 serves to reduce the temperature coefficient of the thermistor per se which is about 4% per degree centigrade to that required by the liquid, i.e. about 2% per degree centigrade.

Connected to the high voltage side of resistors 18 and 20 are series amplifiers 36 and 38 which amplify the voltage across resistors 18 and 20 which is directly proportional to the electrical conductivity of the liquid in the cell bore 11. The output of amplifier 38 is supplied to a phase sensitive rectifier 40 which is also supplied with a reference voltage from the output of amplifier 24. The unsmoothed output of rectifier 40 is then supplied to integrator network 42 comprising amplifier 44 shunted by capacitor 46. The d.c. voltage output frm the network 42 is directly proportional to the liquid conductivity being measured and can be displayed on a meter or can be further amplified and converted to d.c. current proportional to the conductivity being measured and suitable for transmission. Alternatively the d.c. voltage output from the network 42 can be used for set point controls within the instrument.

When a limited range span is required (for example for dialysate monitoring in artificial kidney machines where a range for example of 10 to 16 milliSiemens per centimetre is monitored) it is desirable to remove the lower portion of the instrument range to achieve increased discrimination since the instrument output voltage across resistors 18 and 20 varies from zero to a maximum. This is achieved by supplying amplifier 38 with an additional input backing off voltage from potentiometer 48 proportional to the constant voltage output of amplifier 24. The amplifier 38 acts as a summing amplifier and its output provides voltage which is the difference of its input voltages and the magnitude of which can be controlled by adjustment of the gain of amplifier 38.

If the inputs from amplifiers 24 and 38 to phase sensitive rectifier 40 are in antiphase the output therefrom is of negative magnitude whilst if these inputs are in phase, the output of the phase sensitive rectifier is positive. The origin of the positive output from rectifier 40 is thus referred to the condition when the inputs of amplifier 38 are equal and the positive output increases as the input from amplifier 36 to amplifier 38 exceeds the input thereto from potentiometer 48. By any suitable means, for example, a diode, the input to the circuit 42 can be confined to positive output of the phase sensitive rectifier 40.

An alternative method of temperature compensation involves employing a fixed resistor in place of the thermistor 34 and resistors 18 and 20, the fixed resistor being located in the same position as resistors 18 and 20. A temperature sensing element (which may be a resistance thermometer) is located in the cell and its output is employed to modify the amplitude of the output of amplifier 36 to give temperature compensation.

It will be appreciated that electrodes 1 to 4 operate as current and voltage electrodes in known manner whilst the provision according to the invention of electrodes 5 and 6 has the effect, in the case of electrode 5, of preventing leakage current flowing from electrode 1 whilst electrode 6 provides an earth return for leakage current flowing from electrode 5. Accordingly, leakage current from electrode 5 does not affect the conductivity measurement taken by electrodes 1 to 4. Also, no leakage current flows from electrode 5 to surrounding pipe work since this is prevented by the earth return afforded by electrode 6.

The equal spacing between electrodes 1 and 4, between electrodes 1 and 5 and between electrodes 5 and 6 has the effect, since electrodes 1 and 5 are at the same potential as are electrodes 4 and 6, that current densities in the paths between electrodes 5 and 6 and between electrodes 1 and 4 are substantially equal. Thus the voltage profiles between electrodes 5 and 6 and electrodes 1 and 4 are similar and current leakage between electrodes 1 and 5 is minimised.

The criteria for spacing of the voltage electrodes 2 and 3 are that it is desirable, in order to save on amplification, to have as large as possible a voltage output from these electrodes and that the voltage gradient between these electrodes should be substantially linear. It is further desirable that the spacing should correspond with the calibration constant of the cell. Because of the non-linearity of the voltage gradient in the electrode region, it has been found that the criteria referred to are optimally satisfied by mutual spacing of the voltage electrodes 2 and 3 at a distance which is half the spacing of and symmetrical with respect to the current electrodes 1 and 4.

We claim:

1. A measuring cell of the kind set forth for measuring electrical conductivity of liquids, wherein there are provided electrodes of co-axial form, namely, a first and fourth electrode which constitute current electrodes for connection to a controllable a.c. current supply, a second and third electrode between the first and the fourth electrodes constituting voltage electrodes adapted for connection to a high input impedance amplifier means provided with means for employing the output of the amplifier means to control the a.c. current supply to maintain sensibly constant the voltage at the voltage electrodes, characterised by a fifth electrode of annular form co-axial with the first and fourth electrodes, and means including a buffer amplifier connecting the fifth electrode to the first electrode and presenting a high impedance to the first electrode and a low impedance to the fifth electrode and located on the side of the first electrode remote from the fourth and voltage electrodes.

2. A measuring cell as claimed in claim 1, characterised by a sixth electrode which is of annular form co-axial with the fifth electrode and located on the side thereof remote from the first to the fourth electrodes, the sixth electrode serving, when connected together with the fourth electrode to earth, as a return path for leakage current flow from the fifth electrode.

3. A measuring cell as claimed in claim 2, characterised in that the axial spacings between the first and fourth, the first and fifth and the fifth and sixth electrodes are sensibly equal.

4. A measuring cell as claimed in claim 3 characterised in that the second and third electrodes are located symmetrically between the first and fourth electrodes which are mutually spaced by approximately twice the spacing of the second and third electrodes.

5. A measuring cell of the kind set forth for measuring electrical conductivity of liquids, wherein there are provided electrodes of co-axial annular form, namely a first and fourth electrode which constitute current electrodes connected to a controllable a.c. current supply, a second and third electrode between the first and the fourth electrodes constituting voltage electrodes, a high input impedance amplifier means connected to the voltage electrodes, means for employing the output of the amplifier means to control the a.c. current supply to maintain sensibly constant the voltage at the voltage electrodes, and means for measuring the current supplied to the first and fourth electrodes by the controllable a.c. current supply, including a fifth electrode of annular form co-axial with the first and fourth electrodes connected to the first electrode by way of a buffer amplifier presenting a high impedance to the first electrode and low impedance to the fifth electrode and located on the side of the first electrode remote from the fourth and voltage electrodes.

6. A measuring cell as claimed in claim 5, characterised in that the fourth electrode is earthed.

7. A measuring cell as claimed in claim 6, characterised in that a sixth electrode which is of annular form co-axial with the fifth electrode is located on the side thereof remote from the first to the fourth electrodes, the sixth electrode serving, when connected together with the fourth electrode to earth, as a return path for leakage current flow from the fifth electrode.

8. A measuring cell as claimed in claim 6, characterised in that the axial spacings between the first and fourth, the first and fifth and the fifth and sixth electrodes are sensibly equal.

9. A measuring cell as claimed in claim 8, characterised in that the second and third electrodes are located symmetrically between the first and fourth electrodes which are mutually spaced by approximately twice the spacing of the second and third electrodes.

10. A measuring cell as claimed in claim 7, characterised in that means are provided for temperature compensating an output voltage representative of the current passing through the current electrodes.

11. A measuring cell as claimed in claim 10, characterised in that the temperature compensating means comprise a thermistor located in the cell and disposed in series with a resistor across which and the thermistor the output voltage representative of the current passing through the current electrodes is measured.

12. A measuring cell as claimed in claim 11, characterised in that a resistor is provided in parallel with the thermistor to reduce the temperature coefficient thereof.

13. A measuring cell as claimed in claim 5, characterised in that circuit means are provided for subtracting a backing-off voltage proportional to the output voltage of the high input impedance amplifier means from an output voltage representative of current passing through the current electrodes.

* * * * *